United States Patent [19]
Leiper

[11] Patent Number: 6,128,002
[45] Date of Patent: *Oct. 3, 2000

[54] SYSTEM FOR MANIPULATION AND DISPLAY OF MEDICAL IMAGES

[76] Inventor: Thomas Leiper, 216 Cascade Rd., Stamford, Conn. 06903

[*] Notice: This patent is subject to a terminal disclaimer.

[21] Appl. No.: 08/887,906

[22] Filed: Jul. 3, 1997

Related U.S. Application Data

[60] Provisional application No. 60/021,359, Jul. 8, 1996.

[51] Int. Cl.⁷ ....................................................... G09G 5/00
[52] U.S. Cl. ........................................... 345/156; 345/161
[58] Field of Search ..................................... 345/156, 157, 345/328, 327, 437, 774, 330, 329, 341, 1, 2, 123; 704/225, 233, 239, 275, 270, 201; 386/53, 54, 1.25, 46, 96; 353/25

[56] References Cited

U.S. PATENT DOCUMENTS

| | | |
|---|---|---|
| 4,599,489 | 7/1986 | Cargile . |
| 4,622,013 | 11/1986 | Cerchio . |
| 4,642,621 | 2/1987 | Nemoto et al. . |
| 4,647,916 | 3/1987 | Boughton ................................ 345/123 |
| 4,764,965 | 8/1988 | Yoshimura et al. . |
| 5,019,976 | 5/1991 | Chiu et al. . |
| 5,072,408 | 12/1991 | Ueda ......................................... 353/25 |
| 5,077,666 | 12/1991 | Brimm et al. . |
| 5,099,846 | 3/1992 | Hardy . |
| 5,197,052 | 3/1993 | Schroder et al. . |
| 5,220,611 | 6/1993 | Nakamura et al. . |
| 5,235,510 | 8/1993 | Yamada et al. . |
| 5,272,760 | 12/1993 | Echerer et al. . |
| 5,274,759 | 12/1993 | Yoshioka . |
| 5,293,313 | 3/1994 | Cecil et al. . |
| 5,313,567 | 5/1994 | Civanlar et al. . |
| 5,365,500 | 11/1994 | Park ........................................... 386/46 |
| 5,402,518 | 3/1995 | Lowery .................................... 704/201 |
| 5,414,808 | 5/1995 | Williams ................................. 345/328 |
| 5,452,416 | 9/1995 | Hilton et al. . |
| 5,477,511 | 12/1995 | Englehardt . |
| 5,481,645 | 1/1996 | Bertino et al. . |
| 5,485,171 | 1/1996 | Copper et al. . |
| 5,519,809 | 5/1996 | Husseiny et al. ....................... 704/270 |
| 5,748,930 | 5/1998 | Prakash ................................... 345/330 |
| 5,774,841 | 6/1998 | Salazar et al. .......................... 704/225 |
| 5,831,664 | 11/1998 | Wharton et al. ............................ 345/1 |

FOREIGN PATENT DOCUMENTS

| 4-261579 | 9/1992 | Japan ......................................... 345/1 |
|---|---|---|

OTHER PUBLICATIONS

Alan Simpson, Mastering Word Perfect 5.1 or 5.2 for Windows, pp. 407, 453–455, 1993.
Robert Corwart, Mastering Windows 3.1, pp. 88–90, 1993.
Cowart, Mastering Window 3.1, Special Edition, pp. xxx-iv–xxxv, 235–256 and 885–887, 1993.

*Primary Examiner*—Chanh Nguyen
*Attorney, Agent, or Firm*—St. Onge Steward Johnston & Reens LLC

[57] ABSTRACT

A system for manipulation and display of medical images, comprises an interpretation unit comprising a computer system with an image display unit(s) providing a main viewer and at least one auxiliary clipboard viewer; and a handheld controller. The controller has finger operated dictation and display controls to operate display a series of images in the main viewer. Dictation may be entered in a microphone contained in the controller and digitally recorded in the computer system. A hand held controller for selecting an image displayed in the main viewer and displaying the image in the clipboard viewer are provided to permit assembly of summary studies of medical images, display of side by side comparisons of different series of images. The stored dictation may be synchronized with the images displayed at the time of dictation to provide for a multimedia playback of the dictation and images.

39 Claims, 5 Drawing Sheets

SYSTEM FOR MANIPULATION AND DISPLAY OF MEDICAL IMAGES

This application is based on, and I claim priority rights under 35 U.S.C. §119(e) from, U.S. Provisional patent application Ser. No. 60/021,359, filed Jul. 8, 1996.

FIELD OF THE INVENTION

The present invention relates generally to the field of computerized image acquisition, management and display in medical applications, and more particularly to the field of radiology equipment.

BACKGROUND OF THE INVENTION

Radiographic images, such as X-ray films, and Magnetic resonance imaging ("MRI") and computerized tomograph (CT) transparencies have traditionally been reviewed by a diagnosing physician such as a radiologist on a film viewer, on which a series of images in a patient study are displayed in groups of two or more. Different image series, generated by processing the data captured during a patient scan in different ways, are typically provided. The different image series may display the same portions of the patient's anatomy but processing reduces the amount of information in the image to allow for films having sufficient pixel depth to provide the detail needed for diagnosis in the tissue of interest. The film viewer may be a static light box or a motorized film viewer. A motorized film viewer consists of vertically positioned light boxes and an endless belt on which the films are mounted and which passes the films in front of the light boxes. Motorized film viewers are controlled by the radiologist using foot pedals which activate the motorized viewer to cause the films to be moved to the left or to the right (or in some cases, up and down) to permit viewing of the desired portions of the film series. The images are usually presented in a standard sequence, usually in the order of image capture. The radiologist will typically dictate a medical study into a tape recorder while viewing the films, for later transcription. The films and transcribed dictation are stored in a patient's file.

Filmless image systems have also been proposed and used. Filmless systems have been used in connection with handling both MRI images, and computer tomography images generated by processing X-ray image data to generate a series of "slices" through the human body. Such systems historically have presented all the image data captured by the MRI or tomography equipment, as opposed to in film images (where the medical technician will expose films only for selected series of images of clinical interest). This mass of information has proven unwieldy to review and consider, as instead of filtering the image data through the selection of a skilled technician, all the image data is presented to the diagnosing physician. Another disadvantage of this approach is that it does not provide an "image of record," that is, the basic image(s) relied on by the physician in making the diagnosis. Given the limitations of the image processing equipment, it took a significant amount of time to review the numerous image series. Such systems are far less efficient than the conventional light boxes, which allowed the radiologist to rapidly review numerous series of images to find the few images showing the pathological condition of interest. Other filmless systems have been proposed in which a series of images are presented to the diagnosing physician simultaneously. One such system is described in Hilton, U.S. Patent No. 5,452,416.

However, all of these systems have proven awkward in actual use, as they require use of mouse, keyboard, trackball or other device to navigate through the image series. These control devices severely impair the diagnosing physician's ability to concentrate on the images presented and to relate the images to his knowledge built up through years of practicing medicine. The constant need to correctly position and actuate a mouse and trackball to navigate through images has made the use of such systems far less efficient than conventional film systems. In conventional film systems, the image navigation is effortless, requiring no more than movement of the eyes over a wall filled with film images, allowing the diagnosing physician to concentrate on the real work of interpreting the medical images to reach a diagnosis. Such control devices thus limit the fluid navigation by the diagnosing physician through the image series, and tie the physician to a single position. These control devices are also awkward for a diagnosing physician who may need to refer to materials such as textbooks or prior film-based medical studies for comparison. These devices also may impede the physician's ability to easily dictate the medical study, as most dictation equipment requires a handheld recorder or microphone, thus requiring the physician to either put down and pick up the microphone each time he needs to activate the mouse or trackball to see further images. Alternatively, the physician might learn to work two handedly, but this creates additional complications, for example, if the physician also desired to turn pages in or otherwise refer to a text or other reference material.

SUMMARY OF THE INVENTION

It is an object of the invention to provide a apparatus and method for annotation and navigation of electronic images and documents that increases the diagnosing physician's efficiency in using the system.

It is an object of the invention to provide such an apparatus that can be operated single handedly. It is an object of the invention to provide such a system which permits the diagnosing physician to move around in a work area to retrieve reference works, view past studies, or do other things while at the same time continuing with the medical study of the images.

These objects, and other objects as disclosed in this application, are achieved by an apparatus for audio dictation and navigation of electronic images for use with a personal computer system. The computer system is provided with at least one image display unit, random access memory, means for digital data storage, and an analog to digital conversion system. The apparatus comprises a handheld wireless controller having a combination of controls serving as an image control actuator and a dictation actuator. The image control actuator is operable to transmit wireless control signals to a wireless control signals receiving unit operably connected to the computer system to cause the computer system to display each one of a series of electronic images, in sequential order, and to select display of each next image or next preceding image, and to cause display of related image series in sequential order, and to select display of each next image series or next preceding image series. The dictation actuator is operable to activate wireless transmission of voice signals, generated by a microphone, to a wireless voice signals receiving unit operably connected to the computer system to cause the computer system to convert the voice signals to digital signals and to record the digitized voice signals as digital audio files in the means for digital data storage, and to permit selective playback of such files. Further details of the invention are described below.

BRIEF DESCRIPTION OF THE DRAWINGS

The foregoing aspects and other features of the invention are explained in the following description, taken in connection with the accompanying drawings, wherein.

DETAILED DESCRIPTION OF THE INVENTION

Figure 1:
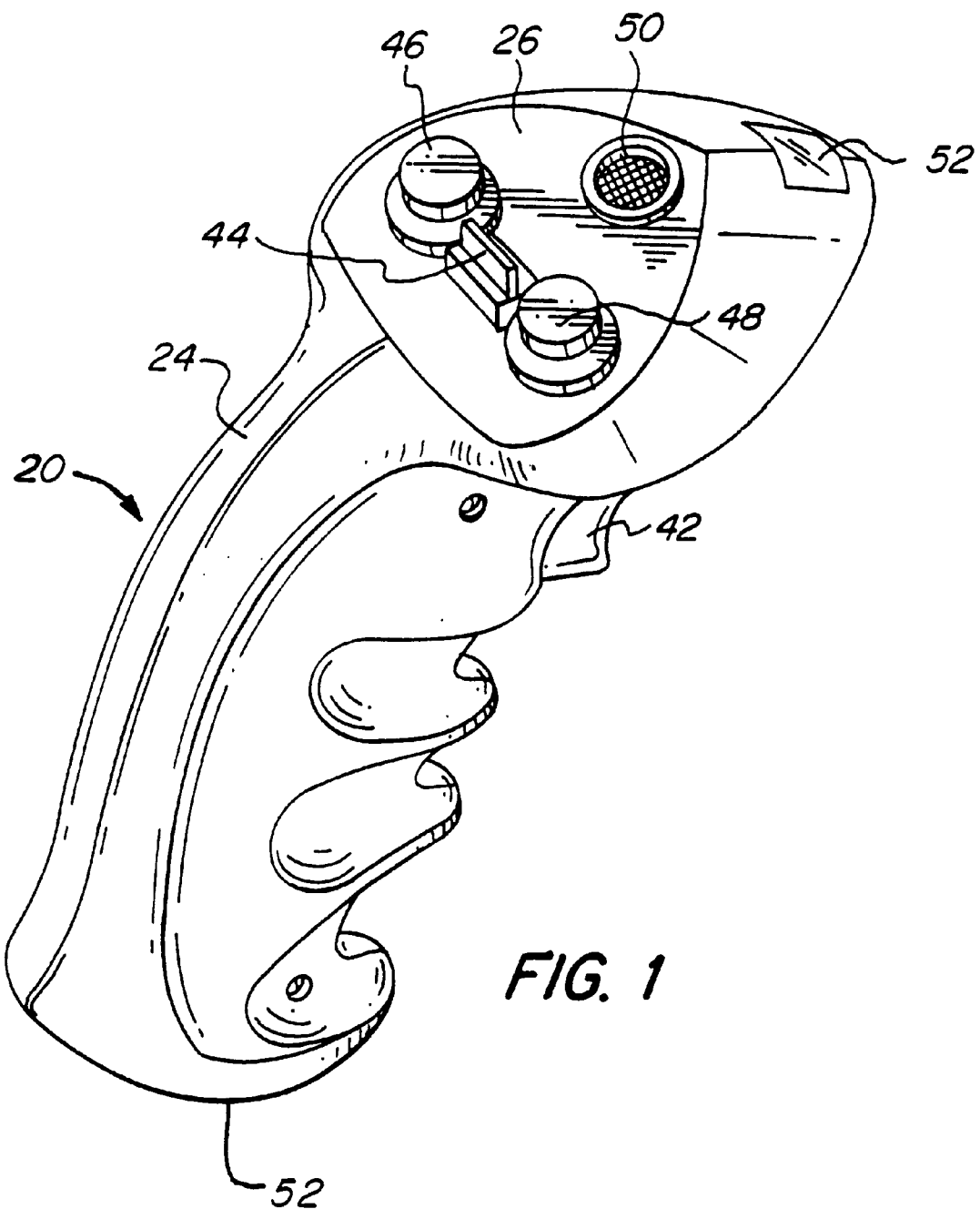
FIG. 1 is a top rear perspective view of a handheld apparatus for audio dictation and navigation of electronic images and documents in accordance with one embodiment of the invention.
Figure 2:
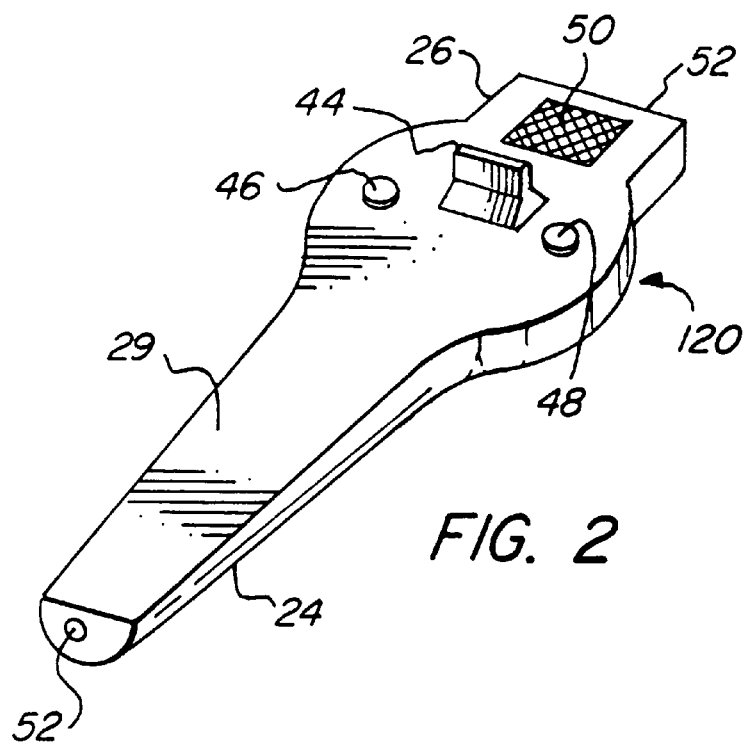
FIG. 2 is a top rear perspective view of a handheld apparatus for audio dictation and navigation of electronic images and documents in accordance with another embodiment of the invention.
Figure 3:
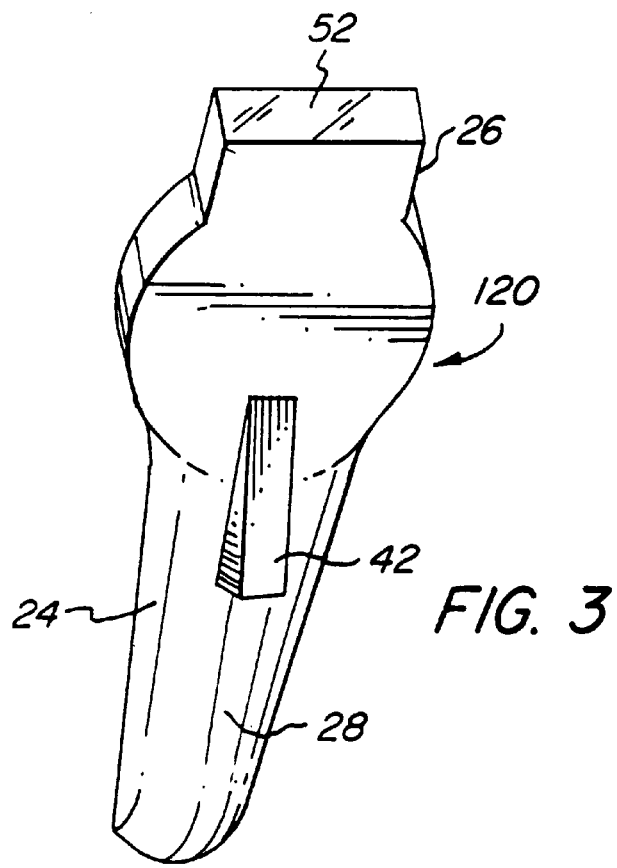
FIG. 3 is a bottom front perspective view of the handheld apparatus for audio dictation and navigation of electronic images and documents of FIG. 2.

Referring to FIGS. 1–7, where like numbered elements in the drawings represent the same elements, a handheld controller 20 for audio dictation and navigation of electronic images and documents is shown in FIG. 1, and another embodiment of such a controller is shown in FIGS. 2 and 3 as 120.

Controllers 20, 120 comprise two significant control subsystems. An image control subsystem permits navigation among the images to be displayed by a viewing unit. A dictation subsystem operates to receive voice dictation. Preferably, a wireless transmitter subsystem transmits commands from the image control subsystem and the dictation control subsystem to a personal computer based interpretation unit 22.

Figure 4:
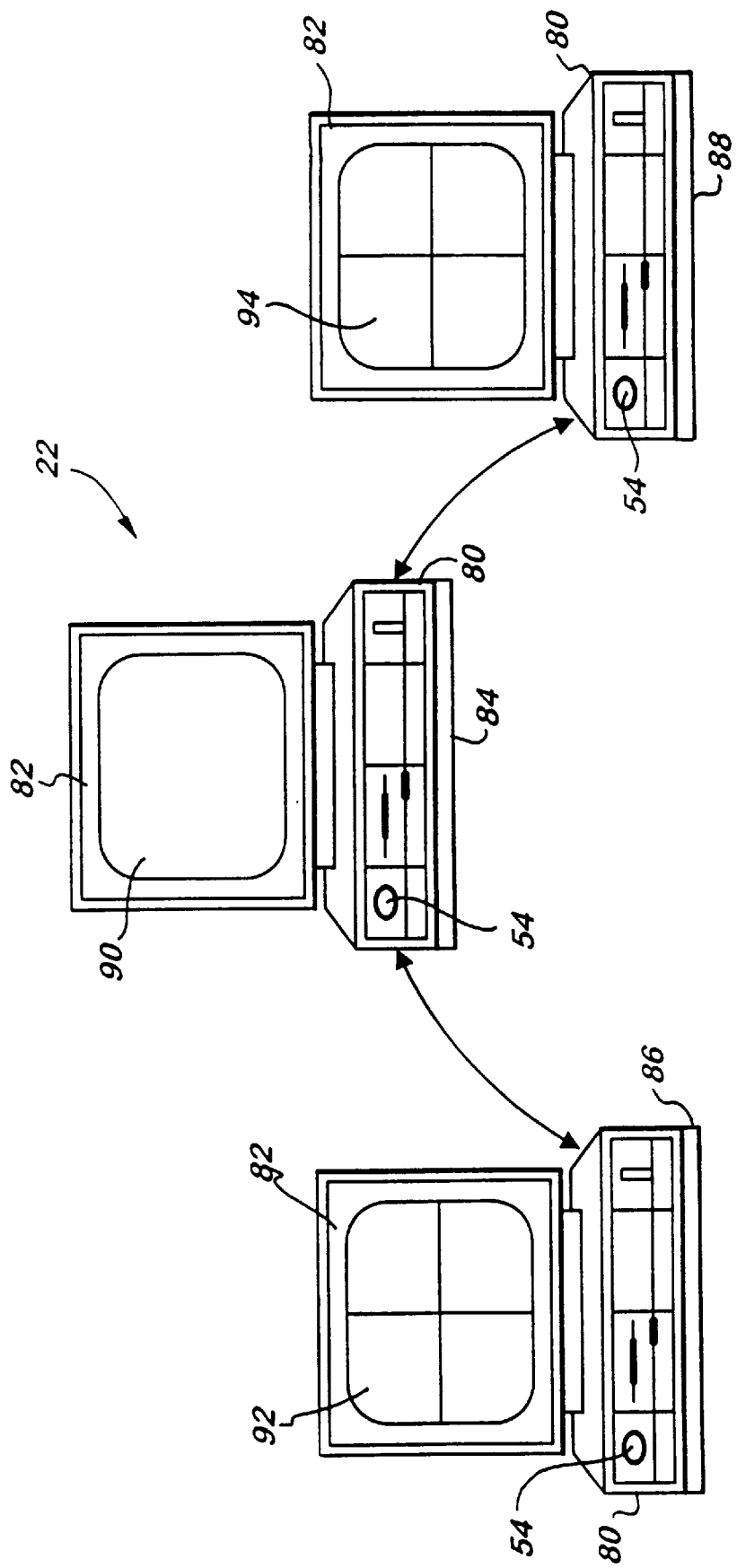
FIG. 4 is a front schematic illustration of computers of an interpretation unit for use with the handheld apparatus of FIGS. 1, 2 and 3.
Figure 5:
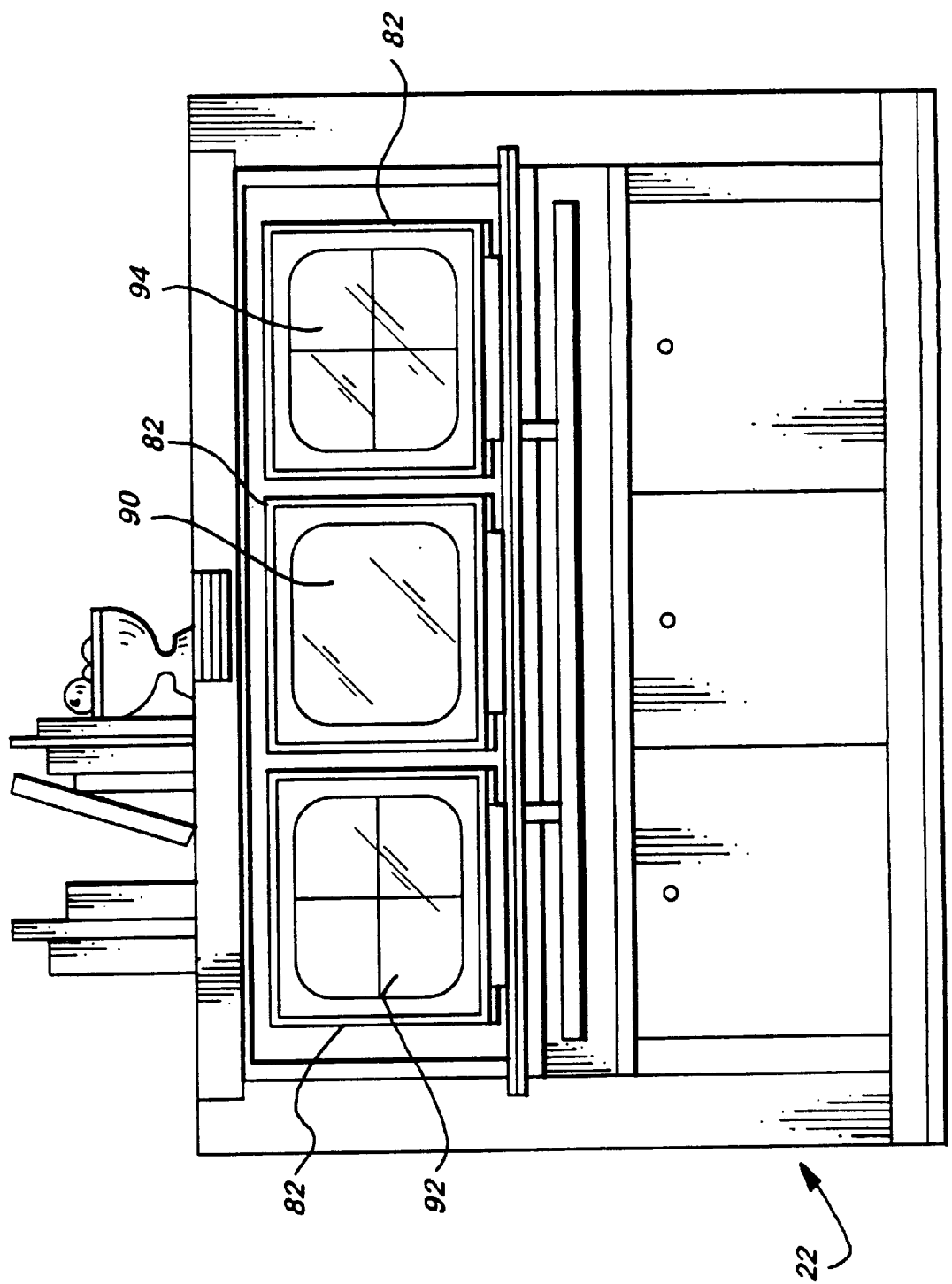
FIG. 5 is a front elevation view of an embodiment of an interpretation unit.

Referring now to FIGS. 4 and 5, the interpretation unit 22 is preferably provided with at least one conventional personal computer or workstation system 80. Most preferably, interpretation unit 22 comprises three conventional personal computer systems 80 which are linked together by a network system. Each personal computer system 80 is preferably a conventional personal computer such as an Intel processor based system running a Windows 95 or Windows NT operating system. Each personal computer system 80 includes an image display unit 82 such as a 20 inch by 20 inch 0.28 dpi non interlaced monitor, random access memory (preferably a minimum of 32 megabytes, and more preferably 128 megabytes), means for digital data storage such as a hard disk drive, and an analog to digital conversion system for converting analog audio signals to digital format. The use of three linked personal computers provides a simple and effective way of driving three separate monitors, which can be independently controlled by the handheld controllers 20, 120 or which can be controlled by the handheld controllers 20, 120 via a selected "master" personal computer 84, with the flanking left personal computers 86 and right personal computer 88 acting as "slave" computers under the control of the "master" computer 84.

In the present invention, various fields of view are contemplated, including a main viewer 90, a left clipboard viewer 92, and a right clipboard viewer 94. As described below, the main viewer 90 will display an image which is then being studied, and the left and right clipboard viewers 92 and 94 serve auxiliary display functions.

In an embodiment of the interpretation unit 22 in which three personal computers are networked together, the monitor of the master computer 84 acts as the main viewer 90, the monitor of the left slave computer 86 will act as a left clipboard viewer 92 and the monitor of the right slave computer 88 will act as the right clipboard viewer 94. However, the viewers 90, 92 and 94 may also be implemented as separate windows displayed on a single monitor if interpretation unit 22 comprises a single personal computer or workstation. In addition, since patient medical images at this time generally consist of black and white images, it would also be possible to implement the three viewers as separate monitors driven by a single personal computer or workstation by appropriate software to drive each monitor in one of the R,G,B (red, green, blue) channels of the RGB color model.

Figure 6:
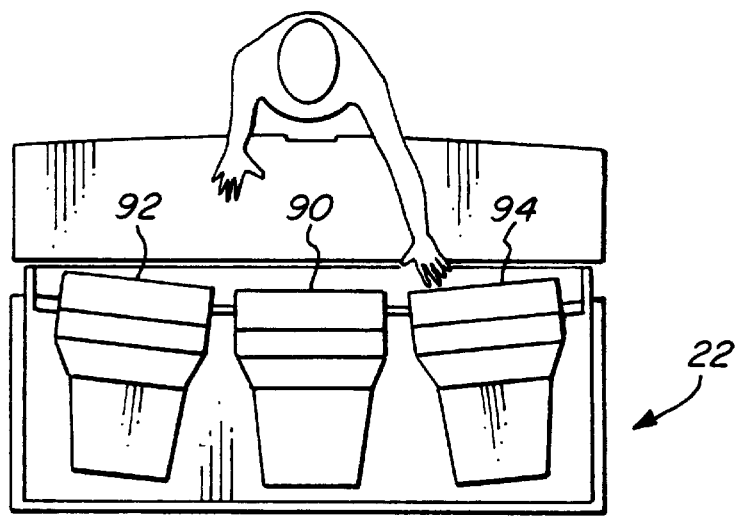
FIG. 6 is a top plan view of the monitors of an interpretation unit positioned for use by a single person.
Figure 7:
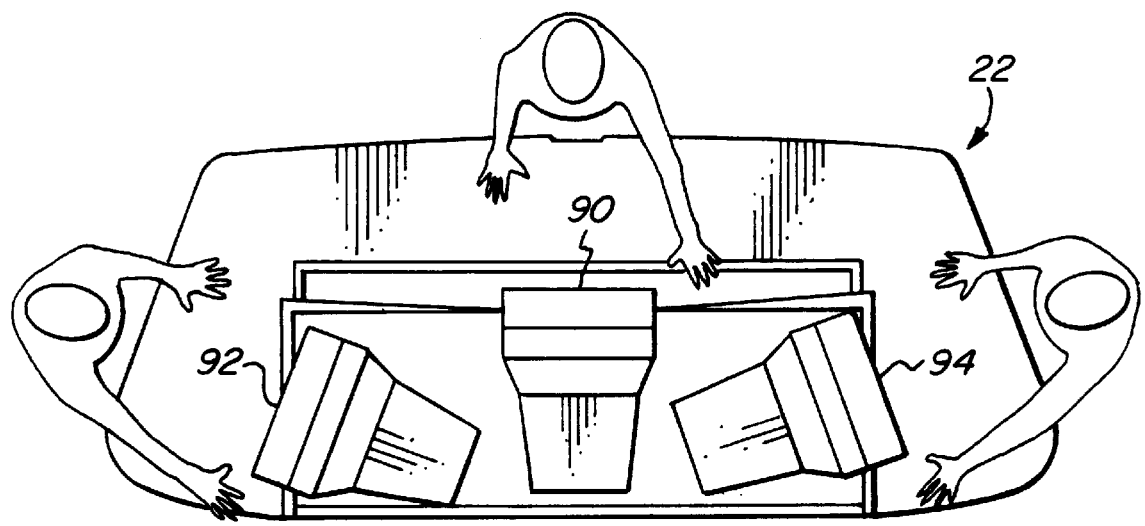
FIG. 7 is a top plan view of the monitors of an interpretation unit positioned for use by multiple persons.

In a preferred embodiment, the three monitors of interpretation unit 22 are mounted on a pivoting mountings, as shown in FIGS. 6 and 7. The pivoting mountings position the main viewer monitor 90 in a central position, with the left and right clipboard viewer monitors 92 and 94 angled inwardly to provide a convenient viewing of all three monitors simultaneously, as shown in FIG. 6. The pivoting mountings are also designed so that the left and right clipboard viewer monitors may be pivoted outwardly, to allow for use of the left and right clipboard viewer monitors 92 and 94 as separate main viewers by other medical personnel, as shown in FIG. 7.

Interpretation unit 22 will have installed in it a "Viewer" application software running on Windows 95 or Windows NT that responds to the diagnosing physician's use of the controllers 20, 120 to implement the commands transmitted from controllers 20, 120. Where interpretation unit 22 consists of three separate computers, each computer will have the "Viewer" software loaded on it, allowing each computer and its associated monitor to be simultaneously used by different persons if desired. The use of separate computers with "Viewer" software provides backup systems in the event of the failure of the "master" computer 84.

In the expected environment of use, the interpretation unit 22 will have received a digital "folder" for the patient to be diagnosed. The "folder" will contain patient identifying information, a patient medical history and/or chart; and a series of digital images to be reviewed by the diagnosing physician. Unlike current filmless systems, the patient images stored in the folder will be images selected by a skilled technician in the same way as is now done in conventional radiology film systems. The images in the patient file will be captured at the MRI or other imaging unit by placing a suitable digitizing tablet in the location where films are exposed by the technician. The exact same procedures as in selecting images for film exposure will apply to the filmless images to be captured for use in the present invention. The digital images are preferably provided in a bitmap format, although other formats may be used.

The patient "folder" will typically be named with the name of the patient, e.g. "John Smith." The interpretation unit 22 may receive such patient information via a hospital network, or a modem transmission, or directly from an image capture device such as a MRI unit.

Controller 20 uses a pistol grip with a control end 26 located in an upper end, similar in appearance to a computer joystick used for playing computer games. Controller 120 is a more elongate handheld device with a control end 26 at one end. In the specification following the term "controller 20" shall be used to refer to both controllers 20 and 120, as the functions thereof are identical, the sole difference being in their shape.

Controller 20 is preferably shaped to be comfortably held in one hand. At control end 26 of case 24 are provided the controls for operating the image control subsystem and the dictation control subsystem.

In the preferred embodiment, the controller 20 has only four switch elements or assemblies to operate as the dictation control and the image display control: a trigger switch 42 located at the underside 28 of controller 20; a pressure switch 44 located on the upper surface 29 of controller 20; and a left toss button 46 located on the upper surface 29 of controller 20 to the left of pressure switch 44; and a right toss button 48 located on the upper surface 29 of controller 20 to the right of pressure switch 44. With reference to FIG. 1, the trigger switch 42 is located where it may be actuated by the forefinger of the user, while the pressure switch 44 and the left and right toss buttons are located on the upper surface of controller 20 where they may be actuated by the user's thumb. These four switch elements or assemblies provide all necessary inputs to achieve the navigation of images and dictation control. If desired, of course, additional buttons and controls may be added, but it is expected that a minimum of controls will provide the most reliable and user friendly control. The present invention desirably has no more than six switch elements or assemblies for operation of all necessary functions. The reduction of controls is achieved in the present invention by allowing for different types of inputs to each switch assembly, such as double clicking or pressure sensitive switches, that allow for different outputs for each input. This is also achieved in the present invention by providing for the different switch assemblies to operate different functions depending on the current mode of operation of the image display and the audio dictation, or combination thereof, at the time of the input to the control.

It is to be appreciated that other switch elements may be substituted for the preferred switch embodiments described above in connection with the controller 20. For example, in an alternative embodiment, the functions of pressure switch 44 and left and tight toss buttons 46 and 48 described below may be implemented in a joystick type control that is movable from front to back and left to right, or by a four way rocker switch, or a thumbwheel, or a tiny trackball, or a sensitive touchpad, or set of directional arrow keys located in the controller 20. Such variations are all within the scope of the invention.

In addition to the control switches 42, 44, 46, and 48, controller 20 is provided with a microphone 50 to receive voice dictation and convert the dictation to appropriate electrical impulses. In another embodiment, controller 20 may have a jack 52 for receiving a clip-on microphone instead of, or in addition to, the microphone in the controller 20. Microphone 50 is preferably located on the upper surface 29 of controller 20 at its control end 26.

Controller 20 may be attached to interpretation unit by suitable electrical cabling, however, in the preferred embodiment, controller 20 is a wireless unit that remotely communicates with interpretation unit 22. Such wireless systems are known in the art and may include radio frequency, infrared, or other wireless communications systems. Preferably, controller 20 is provided with a infrared transmitter 52 at its control end 26 for communication with the interpretation unit 22. In such case, the various keyboard interrupts and/or mouse interrupts generated by the controller 20 are communicated via modulated infrared beams transmitted from the infrared transmitter 52 to infrared receivers 54 associated with the computers or workstations of interpretation unit 22 to cause the desired actions. In addition, voice dictation received in microphone 50 and converted to electrical signals are also communicated from the infrared transmitter 52. If desired, a single transmitter 52 may serve to communicate both the control signals and the dictation signals to the infrared receiver, or separate infrared transmitted may be used. In a wireless embodiment, controller 20 is provided with a power source such as suitable batteries to power the functions of the controller 20.

The control switches 42, 44, 46 and 48 generate keyboard interrupt and mouse control signals that control the interpretation unit 22. Such keyboard interrupt and mouse control signals are conventional signals in operation of personal computer operating systems which are generated, respectively, upon the entry of particular keystrokes or clicking the mouse buttons. In a conventional system, for example a Microsoft Windows operating system, event routines are actuated upon pressing a keyboard key as follows: the keyboard chip transmits a message, that a key or combination of keys are pressed, to a buffer, which notes the key and transmits a message identifying an "onkeydown" routine and the key or key combination pressed to the operating system. The operating systems receives this message and posts a message to all open programs when a keyboard interrupt is received; and the program which is the active program (known as the program which has the "focus") responds to the keyboard input. Upon release of the key on the keyboard, the key chip transmits another key indication; the buffer notes the key and transmits a message identifying an "onkeyup" and the key or key combination pressed to the operating system, which then again transmits this message to all open programs, and the active program responds thereto. In the present invention, the controller switches actuate such keyboard interrupts to instruct a "Viewer" application software running on one or more of the master and slave computers 84, 86, and 88.

It is to be appreciated that with the present invention, the controller 20 is intended to be the only necessary control, and thus the conventional keyboard and mouse controls may be omitted from the personal computers that constitute the interpretation unit 22. However, of course, if desired, such interface devices may be included in the interpretation unit 22, as for example, if the present invention is implemented in a single computer at a medical office where the computer may be used for other functions besides review of medical images for diagnosis. However, it is expected that when the "Viewer" software for operation of the personal computers in their function as an interpretation unit 22 is running, that the controller 20 will be the only interface device necessary for a diagnosing physician's control of the interpretation unit 22 to review patient images and to dictate a medical study.

In one preferred embodiment, the following switches and combinations of switches actuate the following functions. However, of course, the various functions described below may be assigned to other switches or combinations of switches than described in connection with the preferred embodiment, such different assignments being all within the scope of the invention. As described below, image display control and the dictation control have multiple functions, and at least some of the functions of the image display control and the dictation control are both accomplished through commands generated by actuation of one or more of the switches. The particular control function provided by a switch or combination of switches is dependent on the mode of dictation or mode of image display or combination of modes of dictation and image display at the time of operation of such one or more switches.

The trigger switch 42 actuates the primary functions of the voice dictation system. If the trigger switch 42 is clicked and held down, the microphone 50 is connected to a power source, and a keyboard interrupt is sent to the interpretation unit 22, where the "Viewer" software summons the "audio record" function, and voice dictation by the physician into the microphone is communicated to the interpretation station 22 and is recorded as a digital file.

Recording continues until the trigger switch 42 is released, which is transmitted as a keyboard interrupt that causes the "Viewer" software to summon a "stop audio record" function. A hold down of the trigger switch 42 will initiate the record function whether in stop or playback mode.

The audio record function, as well as rewind, playback and other audio functions described herein are conventional features in the Windows 95 operating system and are not described in detail herein. It is noted that a sound card will be required to cause the analog to digital conversion needed to store the voice dictation as a digital file. Voice dictation received by the interpretation unit 22 is stored as a Windows ".wav" file for playback using the conventional Windows based audio software. The file may be stored locally on the interpretation unit 22 or in a network file server as selected.

The "Viewer" software will automatically save the voice dictation file each time the trigger switch 42 is released. The "Viewer" software will automatically save voice dictation file under a file name such as "Study Dictation.wav." The file will preferably be automatically saved in the patient "folder."

When the audio system is in neither the record nor playback, if the trigger switch 42 is clicked and released, the playback function is activated. In the audio file currently open by the "Viewer" software, the recorded audio file will back up two seconds from the end of the file and then will playback that portion of the file to the end. When the recorded audio file is being played back, actuation of the trigger switch 42 by a click and release stops the playback. Also, when the recorded audio file is being played back, actuation of the trigger switch 42 by two clicks and release causes the "Viewer" software to jump to the end of the recorded audio file.

When the audio system is in neither the record nor playback, if the trigger switch 42 is clicked twice it will initiate a "rewind" sequence, in which the position in the audio file is moved back, with acceleration after an initial period of "rewind". "Rewind" may be halted by clicking trigger switch 42 once.

When the audio system is in playback mode, as a result of a single click of trigger switch 42, toss buttons 44 and 46 can be used to call additional audio dictation functions. For example, the left toss button 44 can be used to toggle through various dictation functions (with a screen display in a small window showing the various functions selected). These functions preferably include (1) insert additional audio; (2) overwrite audio; and (3) delete audio. Once a dictation function is selected, the right toss button 46 may be clicked during the desired position in playback to mark the position of the desired function, and clicked a second time, where applicable, to mark the end of the function. Thus, where insert additional audio is desired, the right toss button 46 will mark the position of the audio insert; and the trigger switch 42 may be activated to record the audio insert. Where overwrite audio is desired, the right toss button 46 may be clicked to mark the beginning of the portion of the audio file to be overwritten, and clicked again to mark the end of the portion to be overwritten, and the trigger switch 42 may be activated to record the audio insert to the overwritten portion. Where delete audio is desired, the right toss button 46 may be clicked to mark the beginning of the portion of the audio file to be deleted, and clicked again to mark the end of the portion to be deleted.

Other dictation switch designs may also be used in the handheld controller 20. For example, the dictation control switch may be a slide switch actuated by forward and rearward motion. In such an embodiment, the standard dictation controls (record, off, play, fast forward, rewind) are actuated by positioning the slide switch along the longitudinal axis of the controller 20. Thus, recording is actuated by positioning the slide switch at the forward position of its travel. Moving the slide switch backwardly actuates the following modes, in order: stop, playback, fast forward, and rewind. Other switch control systems may also be implemented in accordance with the invention.

The audio file comprising the diagnosing physician's dictated study of the patient images may be converted to a text file by a transcriptionist or by use of voice recognition software. At the time of the present invention, it is expected that a transcriptionist will be required to accurately transcribe the dictated study. However, as vendors such as IBM and others continue to improve voice recognition software, that the services of a transcriptionist may be less needed, and that voice recognition software may be used to convert the recorded audio file to a text file.

In a system using a transcriptionist in a distributed network, a central file server will maintain information on the status of the patient folder and the contents thereof, and will forward a copy of the audio to a transcription station to generate the corresponding text file.

The controller 20 also controls the "Viewer" software to permit the physician to review the images of the patient. Pressure switch 44 is the principal control for the image viewing system. Pressure switch 44 is a strain gauge switch that transmits different keyboard keys as keyboard interrupt instructions to the interpretation unit 22 depending on the amount of pressure applied to the switch. In the preferred embodiment, pressure switch 44 is a thumb actuated rocker bar switch that has a default centered position, and which may be pushed forwardly or pulled backwardly, against a bias that will tend to center the pressure switch in its centered position. Forward pushing on the edge 45 of switch 44 will cause the Viewer software to advance through the image series. Backwards pulling thereon will cause the Viewer software to back up through the image series. The different keys transmitted by pressure switch 44 instruct the interpretation station 22 to advance or back up through and display the image series at different speeds.

The image series stored in the patient folder in interpretation unit 22 is preferably stored as multiple files, identified for example as 100010001, 100010002, where the terminal four digits identify the number of the image in the series, and the second through fifth digits indicate the number of the series. Actuation of the pressure switch 44 by a single push will cause the Viewer software to display each image file in numeric order, one image at a time, beginning from the first image of the first series. Actuation of the pressure switch 44 by pushing and holding the pressure switch 44 will cause the Viewer software to scroll through the images. The amount of pressure applied to pressure switch 44 will control the speed at which the Viewer software scrolls through the images in the series. The scrolling of images will halt when the end of an image series is reached (or the end of the set of all images reviewed during the study so far), whereupon the first image of the next series will be displayed, and the scrolling function will be terminated. The user may then step or scroll through the displayed next image series by again activating the pressure switch 44. In the preferred embodiment, the physician will be required to step through the entire sets of image series before rapid scrolling will be permitted. This will help to insure that each image is reviewed initially, to prevent missing a potentially relevant image during rapid scrolling.

A serial display as described above is believed to be the most effective way of presenting the images in the patient file, as it maximizes the diagnosing physician's ability to interpret the image using lower cost, standard size computer monitors. However, it is also possible to present the image information in a matrix format with multiple images displayed in a monitor at one time. Such multiple images may comprise a tiled set of windows, each containing a separate image. In such case, the controls of controller 20 will be as described above, except that in stepping or scrolling through images, the Viewer program will step through the different windows.

However, it is believed that a serial display provides a preferable approach as it will force the physician (particularly the experienced physician) to review all the images presented, without the possibility of skipping over a potentially relevant image. With an experienced physician there is sometimes a temptation to leap to the most relevant image—and to reach the obvious diagnosis. With a serial display, a physician will be less likely to miss the less obvious diagnosis that might be reached after proper review of all images. The serial image display is also helpful to the inexperienced physician who will have a better awareness of the entire image set, and what he is looking at, by virtue of the preceding images already displayed. A final benefit of a serial display approach (as opposed to a multiwindow format) is that it allows presentation of a large image. In comparison to film, which has a quality of very high contrast resolution at a certain luminance, current monitors provide much less resolution. To compensate for the reduced contrast resolution, the spacial resolution is enhanced (the image is made larger) to give the user an image of subjective quality that approaches the resolution provided by film.

The "Viewer" software will also determine if the user has displayed a specific image for a predetermined period of time. If so, the Viewer software will "bookmark" for subsequent return. The "bookmark" may be inserted by adding an appropriate stop in the patient image file, or in a table containing a list of the images, or by storing the filename of the displayed image for later recall. Thus, if the diagnosing physician studies the third image in a first series for a period exceeding the predetermined period of time, then steps forward to the third image of the next series, the physician may jump back to the third image of the first series by pulling back on the pressure switch 44. The "Viewer" software, having bookmarked the third image of the first series, will stop backwards scrolling when that image is displayed. In another embodiment of the invention, images studied for a predetermined period of time may be selected to be automatically tossed to one of the clipboard viewer monitors; and/or tossed images may be auto-bookmarked.

As mentioned above, interpretation unit 22 preferably comprises three separate networked personal computers or workstations, operating a main viewer monitor 90, a left clipboard viewer monitor 92, and a right clipboard viewer monitor 94. In a default mode of operation, the main viewer monitor 90 will have displayed on it the selected displayed image in an image series. The left clipboard viewer 92 will be set up to display a number of images in a tiled format, for example, in a 2×2 matrix of tiled images. Other matrix sizes may be used, however, for better image clarity, a 2×2 matrix size is preferred. A title block will be associated with each displayed image to identify the filename of the image.

The toss buttons 46 and 48 serve two functions. A quick click of a toss button 46 or 48 causes the image currently on view on the main viewer monitor 90 to be separately displayed on the respective clipboard viewer monitor 92 or 94. This is again accomplished by the toss button generating a keyboard interrupt with instructs the "Viewer" program to display the selected image on the selected clipboard viewer monitor, for example, by copying the image to a new file containing images of interest, and displaying the new file. The use of the toss buttons 46 and 48 in this manner also marks the "tossed" image for later use of the comparison function described below. An image that has been "tossed" to a clipboard viewer monitor may be "untossed" (removed from the clipboard viewer) by clicking the toss button for the clipboard viewer when the main viewer monitor 90 has displayed on it the image to be "untossed".

It is anticipated that the right clipboard viewer will generally be used for assembling a summary study containing images of particular medical interest, while the left clipboard viewer will be used as a worksheet for displaying side by side comparisons of different series, or display of prior patient studies for comparison (or consultation as needed without interruption of the present study).

If a toss button 46 or 48 is pressed and held down, it will invoke a "mode selection" function in the main viewer program. The "Viewer" program will display a menu of the various modes on the main viewer monitor or one of the clipboard monitors. In the "mode selection" mode, the pressure switch 44 may be used to cycle through the various modes, accompanied by a display in which a highlighted selection bar down the menu of modes. A mode may then be selected by clicking on the toss button again. Of course, other control schemes may be implemented using the controller 20, for example, upon entering a "mode selection" mode, the toss buttons could be used to cycle through the various modes by clicking the toss buttons to cycle one entry at a time through the various modes, and selection could be made by clicking the trigger switch 42; or the trigger switch 42 could be used to cycle through the various modes and the selection could be made by pressing one of the toss buttons. If the toss buttons are used to cycle through the various modes, one toss button will cycle up through the mode selection menu and the other toss button will cycle down through the mode selection menu. In another embodiment, one toss button might be used to cycle through the mode selection menu and the other toss button would be used to select the particular mode to be implemented. Other mode selection and selection schemes are equally within the scope of the present invention.

The "modes" to be selected from may include one or more of the following functions.

(1) List Patients mode. This will cause the system to display the patient folders so that the folder of a patient to be studied can be selected.

(2) View mode. This will cause the system to return to the default viewing mode with controller 20 controlling the master computer 84 of the interpretation unit 22.

(3) Compare mode. This will cause one clipboard viewer (preferably the left clipboard viewer monitor 92) to display a side-by-side presentation of all images in two series starting with the first marked image in each series. For example, while in view mode, a diagnosing physician could select the third image of the second series and send it to the left clipboard viewer 92 by marking with toss button 46, and could then select a fourth image of the fourth series and send this image to the left clipboard viewer 92 by marking with toss button 46. The images would then be displayed with the third image in the second series in the top left quadrant of the monitor screen, and the fourth image of the fourth series in the top right quadrant of the monitor screen. The diagnosing physician would then summon the compare mode, which would cause the display of all subsequent images to the selected images in a side by side relationship, with the selected images on top, and the subsequent images below.

(4) Annotate mode. The master computer 84 may be set up with a light pen, allowing the diagnosing physician to annotate the patient image displayed on the main viewer 90. The annotated image may then be saved as a separate file from the original image by using toss button 48 to save it to the right clipboard viewer 94, or upon return to view mode. Screen buttons actuated by the light pen may be provided to step forward or back through the image series and to "toss" an annotated image to the left or right clipboard. A submenu may also be established to select the particular image to be annotated.

(5) Left clipboard control. This will cause the controller 20 to be acting on and controlling the left clipboard viewer monitor 92. Thus for example, after invoking the compare function described above, the diagnosing physician could then select left clipboard control and use the controller 20 to step up and down or scroll up and down through the side by side comparison, using the pressure switch 44 and the navigation control.

(6) Right clipboard control. This will cause the controller 20 to be acting on and controlling the right clipboard viewer monitor 94.

(7) Dictation special functions. This menu selection will call a submenu with the insert, overwrite, and delete the dictated audio file functions described above.

(8) End study. This will cause the system to close the open files being viewed, and the dictated audio file, and to save the summary study prepared by the diagnosing physician as a separate file or files.

Other modes might include a main menu mode, to call a main mode selection menu, if, for example, some or all of the above functions or additional functions are established as submenus to be selected; and a Mark image mode to bookmark the image currently on display in the main viewer, or to bookmark other images as may be selected from a submenu, to subsequently implement comparison and other functions. The light pen might also be used by a non-physician technician to operate various other functions of the computer.

When series of images in a patient study is first opened, the clipboards may be used to provide an overview of the study. For example, the left and right clipboard viewers 92 and 94 might first have displayed in them the center image of each series of images. Other modes of initial display may be provided, such as the first and last image of a series, or all of the images in one or more series in the patient image file. In some patient image studies, there is a "scout slice", which is an orthogonal view of the patient anatomy of interest showing the location of the various slices constituting the image series. Where a scout slice is available, it will preferably remain on display, most preferably as the last image on display on the left clipboard viewer monitor 92.

Upon tossing of a first image to a clipboard viewer monitor by the toss function, the initial image display will be cleared. Thus for example, upon invoking the toss function to transfer a copy of the image on the main viewer monitor 90 to the right clipboard viewer monitor 94, the images placed on the right clipboard viewer monitor 94 at initial start-up will be cleared. As noted, it is anticipated that the right clipboard viewer 94 will generally be used for assembling a summary study containing images of particular medical interest, and may include annotated images as described above, while the left clipboard viewer 92 will be used as a worksheet. When the summary study is completed, it will be saved as a separate file from the original patient study. It is also possible to save the summary study in the form of a list specifying the images of particular interest from the original, complete, patient image file. The summary study images will typically be the images pertinent to the medical diagnosis, and may printed, and/or delivered back to a referring physician along with the text file comprising the dictated patient study, either in electronic or hard copy form.

The clipboard viewer monitors may also be used for a comparative image display as described above.

The clipboard viewers 92 and 94 also serve other functions. As noted above with regard to the master computer, one slave computer 86 or 88 may be set up with a light pen, allowing the diagnosing physician to annotate the patient image displayed on the clipboard viewer. In such case, the patient image will most likely be displayed in a full size image, rather than in a tiled matrix of smaller images, although, of course, such a smaller format may also be used. Also, the clipboard viewers 92 and 94 could be used to pull up and review a prior patient study without closing the study in progress, as, for example, if the diagnosing physician receives a telephone call seeking discussion of a past patient study, the diagnosing physician could call up, review, and discuss the past patient study, and then return the clipboard viewer to its slave functions as described above.

Control of the display on the clipboard viewer monitors may be accomplished via controller 20 or by separate controls associated with each of the main and clipboard viewers. When control is transferred to a slave computer, another copy of the "Viewer" software is launched in the slave computer and all functions thereof are available on the slave computer.

The display on the clipboard viewer monitors, as well as on the main viewer monitor, may also be controlled by means of an array of buttons placed on or near the monitors. Such buttons, like controller 20, generate keyboard interrupts that provide the control of the images on the viewer monitor. For example, buttons may be provided that trigger a stepping forwards or backwards, or scrolling forwards or backwards, through the images that are selected for display on the particular monitor. of course, other controls implemented through other interfaces such as a conventional keyboard, mouse, touch screen, light pen interface, and the like may also be used.

As prior noted the various functions described above may be assigned to a switch or combination of switches other than the described switch or combination of switches. In this respect, the invention is designed to provide a "context sensitive" control in which various switch combinations achieve different results. For example, as described above, in a dictation edit/revision mode, the physician will not be likely to need the "toss" or "compare" functions, so that the toss buttons 46 and 48 (or other switch elements) may be assigned dictation control functions instead of their usual toss functions. It would also be within the scope of the invention to disable the image advance and retreat functions of a switch such as pressure switch 44 during a dictation edit mode and to assign dictation control functions to that switch during dictation edit mode. Similarly, as described above, when the "mode selection" menu is displayed, the physician is not likely to need the dictation functions, and the trigger switch 42 may be assigned mode selection functions instead of the usual dictation functions.

A further feature of the present invention is a "multimedia" record function. This function will desirably be implemented automatically whenever the dictation trigger switch is activated, or may be limited to the final "Conclusion" which is conventional at the end of any medical diagnostic dictation, or may be applied in some other summary time period. The "multimedia record function" is to record the images being reviewed by the physician at the time the dictation is recorded, enabling a later playback of the dictation with simultaneous display of the images that the physician reviewed at the time of the dictation. The image display will be synchronized to the dictation so that on playback the precise image being viewed at the time of the specific dictation is displayed. The "multimedia record function" may be implemented by recording the file name of the image on display at the time of particular dictation, which may be embedded into the dictation file as a link or using other conventional techniques for slide show type presentations, or by other file list methods.

The above described serial display system for patient images is believed to be the most efficient and user friendly system that may be implemented. However, other possible control systems may also be implemented in accordance with the invention. In an alternative control system, using a pressure switch having additional left and right switch positions in addition to front and back switch settings, it would be possible to control the "Viewer" software to jump among the different image series. Thus instead of scrolling to the end of an image series to obtain the next series, a diagnosing physician could implement the display of the next preceding series at the same image number as being currently viewed by leftward pressure on the switch, or of the next succeeding series by rightward pressure on the switch. This would permit "lateral" movement among the various patient series. Once a new series sequence was selected, the physician could then scroll forwards or backwards through the series as in the above described serial display embodiment. An adjunct clipboard viewer display might also be provided in such case to provide a matrix containing thumbnail size images of all the images in the patient folder, arrayed in columns, with each column containing the images of a different series. The adjunct clipboard viewer would indicate the image being presented to the main viewer by appropriate highlighting or framing, as an aid to navigation among the images in the study.

Although the foregoing description has described an application of a combined image review/voice dictation function in a controller 20 operating in conjunction with a medical interpretation unit, the present invention has broader application as well. It may be implemented for example in a legal or business environment. For example, using controller 20, an attorney reviewing documents could dictate comments on the documents (as in reviewing electronically stored raster images of production documents in litigation) or revisions to a document (as in revisions to a contract). The images which may be controlled in this fashion may thus include graphic images, text documents, and other electronic files. The controller 20 in the first example would interface with a viewer software that controls viewing of the imaged documents. The controller 20 in the second example would interface with word processing software to insert a comment or margin note in the document for a transcriptionist to later type in the requested changes, or would work in conjunction with a speech to text conversion system to implement the revisions. Similarly, a business person might dictate comments or responses to electronically received faxes, and documents for typing or conversion to text.

The present invention provides an convenient and practical apparatus for review of radiographic medical images with integrated dictation control and has better operational flexibility than any device known in the art.

It is to be appreciated that the foregoing is illustrative and not limiting of the invention, and that various changes and modifications to the preferred embodiments described above will be apparent to those skilled in the art. For example, the invention has application in other fields where it is desired to have a handheld unit that can control image review with dictation abilities, such as in legal and business fields. Such changes and modifications can be made without departing from the spirit and scope of the present invention, and it is therefore intended that such changes and modifications be covered by the following claims.

What is claimed is:

1. A system for manipulation and display of image files, comprising:

an interpretation unit comprising a computer system, said computer system being provided with at least one image display unit, random access memory, means for digital data storage;

said image display unit being provided with a main viewer and at least one auxiliary clipboard viewer;

a handheld controller, said controller having
a finger operated image display control for generating commands for controlling display of medical radiographic image files in said image display unit,
a finger operated dictation control for generating commands for controlling recording and playback of audio dictation, and
means for communicating said commands for controlling display of different medical radiographic image files, said commands for controlling recording and playback of audio dictation to said computer system;

means for displaying a series of image files in said main viewer;

means for selecting an image file displayed in said main viewer and displaying said image file in said clipboard viewer; and means for comparison display, in a side by side relationship in one said clipboard viewer for visual comparison, a first series of image files beginning with an initial first image file selected by the user with subsequent image files automatically selected by said means for comparison display, and a second series of image files beginning with an initial second image file selected by the user with subsequent image files in said second series of image files automatically selected by said means for comparison display.

2. A system in accordance with claim 1, wherein said image display control and said dictation control have multiple functions, and wherein at least some of said functions of said image display control and said dictation control are both accomplished through commands generated by actuation of one or more of first, second, third and dictation switch elements, the particular control function provided by a switch element or combination of switch elements being dependent on a mode of dictation or a mode of image display or combination of modes of dictation and image display at the time of operation of said one or more switch elements.

3. A system in accordance with claim 1, wherein said controller further comprises a microphone for receiving audio dictation and generating electrical signals corresponding to said audio dictation, and said means for communicating further comprises means for communicating said electrical signals corresponding to said audio dictation to said computer system, and said computer system digitally stores said electrical signals, and further, wherein said dictation control is operable to control recording and playback of said digitally stored electrical signals corresponding to said audio dictation.

4. A system in accordance with claim 3, further comprising means for multimedia recording and playback, wherein audio dictation stored in said computer system is indexed to image files displayed in said main viewer at the time when such audio dictation is recorded, whereby playback of said recorded audio dictation is accompanied by display of image files which were on display at the time of recording said audio dictation.

5. A system in accordance with claim 1, wherein said image display control and said dictation control comprise no more than six switch elements.

6. A system in accordance with claim 5, wherein said image display control and said dictation control comprise no more than four switch elements.

7. A system in accordance with claim 1, wherein said main viewer and said clipboard viewer comprise separate monitors.

8. A system in accordance with claim 1 wherein said main viewer and said clipboard viewer comprise separate windows displayed on a single monitor.

9. A system in accordance with claims 1, 7, or 8 wherein there is one said main viewer and two said clipboard viewers.

10. A system in accordance with claim 1, wherein said means for displaying a series of different image files in said main viewer displays said image files one image at a time in a serial order during at least an initial display of said images.

11. A system in accordance with claim 1, wherein said image display control comprises a switch which is operable to generate commands to transfer an image from an image file displayed in said main viewer to at least one said clipboard viewer.

12. A system in accordance with claim 11, whereupon operation of said switch to generate commands to transfer an image file displayed in said main viewer to at least one said clipboard viewer, said switch also generates commands to store an indication for such image file in said computer system, and whereby said computer system causes the display of the image file corresponding to the stored indication upon operation of said display control to generate commands for displaying image files for which an indication has been stored.

13. A system in accordance with claim 1, wherein said image display control comprises a switch which is operable to generate commands to cause said computer system to advance and to back up through a series of image files displayed in said image display unit.

14. A system in accordance with claim 13, wherein said image display switch is responsive to the amount of pressure applied thereto whereby lesser pressures applied thereto generate commands for advancing or backing up through images at a slower rate, and greater pressures applied thereto generate commands for advancing or backing up through images at a faster rate.

15. A system in accordance with claim 1, wherein said computer system stores an indication for an image file which the user of the system displays for a time period exceeding a predetermined time period, and whereby said computer system causes the display of the image file corresponding to the stored indication upon operation of said display control to generate commands for displaying image files for which an indication has been stored.

16. A system in accordance with claims 15 or 12, wherein said commands for displaying image files for which an indication has been stored comprises commands for causing backing up through image files displayed in a display unit at a maximum rate.

17. A system in accordance with claim 1, further comprising means for displaying in said clipboard viewer selected image files from said series of image files upon opening of a patient file containing said series of image files.

18. A system for manipulation and display of image files, comprising:

an interpretation unit comprising three networked computer systems, said computer systems being provided an image display unit, random access memory, means for digital data storage, one of said computer systems acting as master computer and two of said computers acting as slave computers;

said image display units comprising a main viewer associated with said master computer and auxiliary clipboard viewers associated with said slave computers;

a handheld controller, said controller having
 a finger operated image display control for generating commands for controlling display of radiographic medical image files in at least one said image display unit,
 a microphone for receiving audio dictation and generating electrical signals corresponding to said audio dictation,
 a finger operated dictation control operable to generate commands for recording and playback of audio dictation received in said microphone, converted to said electrical signals, and digitally stored in one of said computer systems, and
 means for communicating said commands for controlling display of image files, said commands for controlling recording and playback of audio dictation, and said electrical signals corresponding to said audio dictation to said master computer;

said image display control and said dictation control having multiple functions, at least some of said functions of said image display control and said dictation control being both accomplished through commands generated by actuation of one or more switch elements, the particular control function provided by a switch element or combination of switch elements being dependent on a mode of dictation or a mode of image display or combination of modes of dictation and image display at the time of operation of said one or more switch elements;

means for displaying a series of different radiographic medical image files in said main viewer, said displaying means displaying said image files one file at a time in a serial order during at least an initial display of said image files;

means for selecting an image file displayed in said main viewer and displaying said image file in at least one said clipboard viewer ; and means for comparison display, in a side by side relationship in one said clipboard viewer for visual comparison, a first series of image files beginning with an initial first image file selected by the user with subsequent image files automatically selected by said means for comparison display, and a second series of image files beginning with an initial second image file selected by the user with subsequent image files in said second series of image files automatically selected by said means for comparison display.

19. A system in accordance with claim 18, wherein said computer system stores an indication for an image file which the user of the system displays for a time period exceeding a predetermined time period, and whereby said one of said computer systems causes the display of the image file corresponding to the stored indication upon operation of said display control to generate commands for displaying image files for which an indication has been stored.

20. A system in accordance with claim 18, whereupon operation of said means for selecting an image file displayed in said main viewer and displaying said image file in at least one said clipboard viewer, said selecting and displaying means also generates commands to store an indication for such image file in said computer system, and whereby said computer system causes the display of the image file corresponding to the stored indication upon operation of said display control to generate commands for displaying image files for which an indication has been stored.

21. A system in accordance with claims 19 or 20, wherein said commands for displaying image files for which an indication has been stored comprise commands for causing backing up at a maximum rate through image files displayed in a display unit.

22. A system in accordance with claim 18, further comprising means for displaying in said clipboard viewer selected image files from said series of image files upon opening of a patient file containing said series of image files.

23. A system in accordance with claim 18, further comprising means for multimedia recording and playback, wherein audio dictation stored in said computer system is indexed to image files displayed in said main viewer at the time when such audio dictation is recorded, whereby playback of said recorded audio dictation is accompanied by display of image files which were on display at the time of recording said audio dictation.

24. A system in accordance with claim 18, further comprising a light pen operable connected with said master computer to permit annotation of image files displayed on said main viewer.

25. A system in accordance with claim 18, wherein one/said clipboard viewer is positioned to the right of said main viewer, and another said clipboard viewer is positioned to the left of said main viewer.

26. A system in accordance with claim 25, wherein said left and right clipboard viewers are located on pivotable mounts, whereby said three viewers are locatable to face a central position, and whereby said left and right clipboard viewers are pivotable outwardly to face left and right positions.

27. A system for manipulation and display of image files, comprising:
    an interpretation unit comprising a computer system, said computer system being provided with at least one image display unit, random access memory, means for digital data storage;
    said image display unit being provided with a main viewer and at least one auxiliary clipboard viewer;
    a handheld controller, said controller having
        a finger operated image display control for generating commands for controlling display of image files in said image display unit,
        means for communicating said commands for controlling display of image files to said computer system;
    means for displaying a series of image files in said main viewer;
    means for selecting an image different radiographic medical file displayed in said main viewer and displaying said image file in said clipboard viewer; and
    means for comparison display, in a side by side relationship in one said clipboard viewer for visual comparison, a first series of image files beginning with an initial first image file selected by the user with subsequent image files automatically selected by said means for comparison display, and a second series of image files beginning with an initial second image file selected by the user with subsequent image files in said second series of image files automatically selected by said means for comparison display.

28. A system in accordance with claim 27, wherein said image display control has multiple functions, and wherein at least some of said functions of said image display control is accomplished through commands generated by actuation of one or more of first, second, third switch elements, the particular control function provided by a switch element or combination of switch elements being dependent on a mode of image display at the time of operation of said one or more switch elements.

29. A system in accordance with claim 27, wherein said main viewer and said clipboard viewer comprise separate monitors.

30. A system in accordance with claim 27 wherein said main viewer and said clipboard viewer comprise separate windows displayed on a single monitor.

31. A system in accordance with claim 27, wherein there is one said main viewer and two said clipboard viewers.

32. A system in accordance with claim 27, wherein said means for displaying a series of different image files in said main viewer displays said image files one image at a time in a serial order during at least an initial display of said images.

33. A system in accordance with claim 27, wherein said image display control comprises a switch which is operable to generate commands to transfer an image from an image file displayed in said main viewer to at least one said clipboard viewer.

34. A system in accordance with claim 33, whereupon operation of said switch to generate commands to transfer an image file displayed in said main viewer to at least one said clipboard viewer, said switch also generates commands to store an indication for such image file in said computer system, and whereby said computer system causes the display of the image file corresponding to the stored indication upon operation of said display control to generate commands for displaying image files for which an indication has been stored.

35. A system in accordance with claim 27, wherein said image display control comprises a switch which is operable to generate commands to cause said computer system to advance and to back up through a series of image files displayed in said image display unit.

36. A system in accordance with claim 35, wherein said image display switch is responsive to the amount of pressure applied thereto whereby lesser pressures applied thereto generate commands for advancing or backing up through images at a slower rate, and greater pressures applied thereto generate commands for advancing or backing up through images at a faster rate.

37. A system in accordance with claim 29, wherein said computer system stores an indication for an image file which the user of the system displays for a time period exceeding a predetermined time period, and whereby said computer system causes the display of the image file corresponding to the stored indication upon operation of said display control to generate commands for displaying image files for which an indication has been stored.

38. A system in accordance with claims 37 or 34, wherein said commands for displaying image files for which an indication has been stored comprises commands for causing backing up through image files displayed in a display unit at a maximum rate.

39. A system in accordance with claim 27 further comprising means for displaying in said clipboard viewer selected image files from said series of image files upon opening of a patient file containing said series of image files.

* * * * *